(12) United States Patent
Uchiyama

(10) Patent No.: US 7,852,480 B2
(45) Date of Patent: Dec. 14, 2010

(54) HYDROGEN GAS DETECTION DEVICE

(75) Inventor: Naoki Uchiyama, Hamamatsu (JP)

(73) Assignee: Kabushiki Kaisha Atsumitec, Hamamatsu-Shi (JP)

( * ) Notice: Subject to any disclaimer, the term of this patent is extended or adjusted under 35 U.S.C. 154(b) by 266 days.

(21) Appl. No.: 12/293,267

(22) PCT Filed: Feb. 15, 2007

(86) PCT No.: PCT/JP2007/052755

§ 371 (c)(1),
(2), (4) Date: Sep. 16, 2008

(87) PCT Pub. No.: WO2007/108261

PCT Pub. Date: Sep. 27, 2007

(65) Prior Publication Data

US 2009/0135425 A1 May 28, 2009

(30) Foreign Application Priority Data

Mar. 17, 2006 (JP) .............................. 2006-074735

(51) Int. Cl.
*G01N 21/00* (2006.01)
*G01N 21/55* (2006.01)
(52) U.S. Cl. ...................... 356/437; 356/448
(58) Field of Classification Search .......... 356/432–444
See application file for complete search history.

(56) References Cited

U.S. PATENT DOCUMENTS

| 4,560,444 A | * | 12/1985 | Polak et al. | .................. 205/783 |
| 4,661,320 A | * | 4/1987 | Ito et al. | ...................... 422/86 |
| 4,962,021 A | * | 10/1990 | Meserol et al. | ............ 435/7.92 |
| 4,990,287 A | * | 2/1991 | Bennion et al. | ............. 252/586 |
| 5,783,152 A | * | 7/1998 | Nave | ........................ 422/82.06 |
| 6,006,582 A | * | 12/1999 | Bhandari et al. | ............. 73/23.2 |
| 6,897,960 B2 | * | 5/2005 | DiMeo et al. | ................ 356/437 |
| 7,116,421 B2 | * | 10/2006 | Garcia et al. | ................. 356/437 |

FOREIGN PATENT DOCUMENTS

| JP | 58-079141 A | 5/1983 |
| JP | 60-039536 A | 3/1985 |
| JP | 60-76648 A | 5/1985 |
| JP | 01-320451 A | 12/1989 |
| JP | 07-243973 A | 9/1995 |

(Continued)

OTHER PUBLICATIONS

English Language International Search Report dated Mar. 20, 2007 issued in parent Appln. No. PCT/JP2007/052755.

*Primary Examiner*—Gregory J Toatley, Jr.
*Assistant Examiner*—Jarreas C. Underwood
(74) *Attorney, Agent, or Firm*—Holtz, Holtz, Goodman & Chick, PC

(57) ABSTRACT

In a hydrogen gas detection device, light emitted from a light source is irradiated onto a hydrogen sensor whose reflectance (optical reflectance) varies upon contact with hydrogen gas, and the light transmitted through the hydrogen sensor or reflected by a reflective film of the hydrogen sensor is received by an optical sensor. On the basis of the signal output from the optical sensor and indicative of the amount of light received, the hydrogen gas detection device detects leakage of hydrogen gas.

3 Claims, 5 Drawing Sheets

FOREIGN PATENT DOCUMENTS

| | | |
|---|---|---|
| JP | 09-113501 A | 5/1997 |
| JP | 2003-098147 A | 4/2003 |
| JP | 2003-329592 A | 11/2003 |
| JP | 2004-144564 A | 5/2004 |
| JP | 205-083832 A | 3/2005 |

* cited by examiner

HYDROGEN GAS DETECTION DEVICE

This application is a U.S. National Phase Application under 35 USC 371 of International Application PCT/JP2007/052755 filed Feb. 15, 2007.

TECHNICAL FIELD

The present invention relates to a hydrogen gas detection device for detecting hydrogen gas.

BACKGROUND ART

Hydrogen has been attracting attention as an energy source capable of restraining emission of carbon dioxide. There is a possibility, however, that if hydrogen gas leaks out into the surrounding atmosphere (e.g., an area around a hydrogen gas generation apparatus or hydrogen gas storage apparatus, or a parking lot where motor vehicles using hydrogen as fuel are parked), explosion will be caused. It is therefore necessary that leakage of hydrogen gas should be immediately detected and stopped.

To meet the needs, a hydrogen gas detection device has been contrived in which leakage hydrogen gas is detected by a hydrogen sensor heated by a heater. Hydrogen gas detection devices of this type are disclosed, for example, in Unexamined Japanese Patent Publications No. 2003-098147 and No. 2004-144564.

However, the hydrogen sensors used in these hydrogen gas detection devices cannot detect hydrogen unless they are heated to a high temperature of several hundred degrees Celsius. Thus, the possibility of a hydrogen gas explosion being induced by heat cannot be negated, making it necessary to take measures to prevent such explosion from being caused by the high-temperature heating.

Also, with the above hydrogen gas detection device, although leakage hydrogen gas present around the hydrogen sensor can be detected, it is not possible to detect leakage hydrogen gas over a wide area (space).

DISCLOSURE OF THE INVENTION

The present invention was created in view of the above circumstances, and an object thereof is to provide a hydrogen gas detection device whose hydrogen sensor need not be heated.

Another object of the present invention is to provide a hydrogen gas detection device that does not require measures to be taken to prevent an explosion from being caused by high-temperature heating.

Still another object of the present invention is to provide a hydrogen gas detection device capable of quickly and safely detecting leakage of hydrogen gas preferably over a wide area.

To achieve the objects, the present invention provides a hydrogen gas detection device comprising: a hydrogen sensor whose reflectance varies upon contact with hydrogen gas; a light source for irradiating light onto the hydrogen sensor; and an optical sensor for receiving the light emitted from the light source and transmitted through or reflected by the hydrogen sensor, and for outputting a detection signal.

In a normal state in which no leakage hydrogen gas exists, the hydrogen sensor of the hydrogen gas detection device has high reflectance (or low reflectance). On the other hand, when exposed to an atmosphere containing more hydrogen gas than in the normal state, the reflectance of the hydrogen sensor decreases (or increases).

It is therefore possible to detect leakage of hydrogen gas on the basis of the detection signal output from the optical sensor and indicative of the amount of light received thereby, the light being emitted from the light source and transmitted through or reflected by the hydrogen sensor.

Alternatively, to achieve the above objects, the present invention provides a hydrogen gas detection device comprising: a light source for emitting light; an optical sensor for receiving the light and outputting a detection signal; and a plurality of hydrogen sensors for successively reflecting the light emitted from the light source to transmit the light to the optical sensor, wherein reflectance of each of the hydrogen sensors varies upon contact with hydrogen gas.

With this hydrogen gas detection device, if leakage hydrogen gas reaches the vicinity of any one of the hydrogen sensors, the reflectance of this hydrogen sensor varies. The light from the light source is reflected successively by the multiple hydrogen sensors before reaching the optical sensor, and the amount of light received by the optical sensor varies due to the change of the reflectance. It is therefore possible to detect leakage of hydrogen gas over a wide area where the multiple hydrogen sensors are arranged, based on the detection signal output from the optical sensor and indicative of change in the amount of light received.

Specifically, in the above hydrogen gas detection devices, the hydrogen sensor may include: a substrate capable of transmitting the light therethrough; and a reflective film whose reflectance varies upon contact with hydrogen gas.

More specifically, the reflective film may include: a thin-film layer formed on an obverse or reverse surface of the substrate; and a catalyst layer formed on a surface of the thin-film layer, the catalyst layer hydrogenating the thin-film layer upon contact with hydrogen gas to vary reflectance of the thin-film layer.

Alternatively, to achieve the above objects, the present invention provides a hydrogen gas detection device comprising: a hydrogen sensor including a substrate capable of transmitting light therethrough, a first reflective film formed on one surface of the substrate, a second reflective film formed on an opposite surface of the substrate, an optical input port for admitting light to one end of the substrate, and an optical output port for receiving the light that arrives at an opposite end of the substrate after being input from the optical input port and then reflected alternately by the first and second reflective films, and for allowing the received light to be output to outside of the substrate, wherein reflectance of either one or both of the first and second reflective films varies upon contact with hydrogen gas; a light source for inputting the light to the optical input port; and an optical sensor for receiving the light output from the optical output port and outputting a detection signal.

In this hydrogen gas detection device, when the reflectance of one or both of the first and second reflective films decreases (or increases) due to contact with hydrogen gas, the light (amount of light) output from the optical output port decreases (or increases). Thus, leakage of hydrogen gas can be detected on the basis of the detection signal output from the optical sensor and corresponding to the amount of light received from the optical output port.

Alternatively, to achieve the above objects, the present invention provides a hydrogen gas detection device comprising: a plurality of hydrogen sensors each including a substrate capable of transmitting light therethrough, a first reflective film formed on one surface of the substrate, a second reflective film formed on an opposite surface of the substrate, an optical input port for admitting light to one end of the substrate, and an optical output port for receiving the light that arrives at an opposite end of the substrate after being input from the optical input port and then reflected alternately by the first and second reflective films, and for allowing the received light to be output to outside of the substrate, wherein reflectance of either one or both of the first and second reflective films varies upon contact with hydrogen gas; optical transmission means for cascade-connecting the hydrogen sensors to form an optical circuit; a light source for inputting the light to the optical input port of that one of the cascade-connected hydrogen sensors which is situated at an input end of the optical circuit; and an optical sensor for receiving the light output from the optical output port of that one of the cascade-connected hydrogen sensors which is situated at an output end of the optical circuit, and for outputting a detection signal.

With this hydrogen gas detection device, if leakage hydrogen gas reaches the vicinity of any one of the hydrogen sensors, the light (amount of light) output from the optical output port of this hydrogen sensor varies. Since the multiple hydrogen sensors are cascade-connected by the optical transmission means to constitute the optical circuit, the amount of light reaching the optical sensor via the optical transmission means varies. It is therefore possible to detect leakage of hydrogen gas over a wide area where the multiple hydrogen sensors are arranged, based on the detection signal output from the optical sensor and indicative of change in the amount of light received.

Specifically, in the above hydrogen gas detection devices, the first and/or second reflective film of which the reflectance varies upon contact with hydrogen gas may include: a thin-film layer formed on the corresponding surface of the substrate; and a catalyst layer formed on a surface of the thin-film layer, the catalyst layer hydrogenating the thin-film layer upon contact with hydrogen gas to vary reflectance of the thin-film layer.

As seen from the above, the hydrogen gas detection devices according to the present invention are each adapted to quickly detect change in the reflectance (optical reflectance) of the hydrogen sensor due to contact with hydrogen gas, by detecting change in the amount of light received by the optical sensor. It is therefore unnecessary to heat the hydrogen sensor, and thus, to take measures to prevent explosion from being induced by high-temperature heating. Accordingly, leakage of hydrogen gas can be detected quickly and safely, and where a plurality of hydrogen sensors are used, it is possible to detect leakage of hydrogen gas over a wide area.

BEST MODE OF CARRYING OUT THE INVENTION

Hydrogen gas detection devices according to preferred embodiments of the present invention will be described below with reference to the accompanying drawings.

First Embodiment

Figure 1:
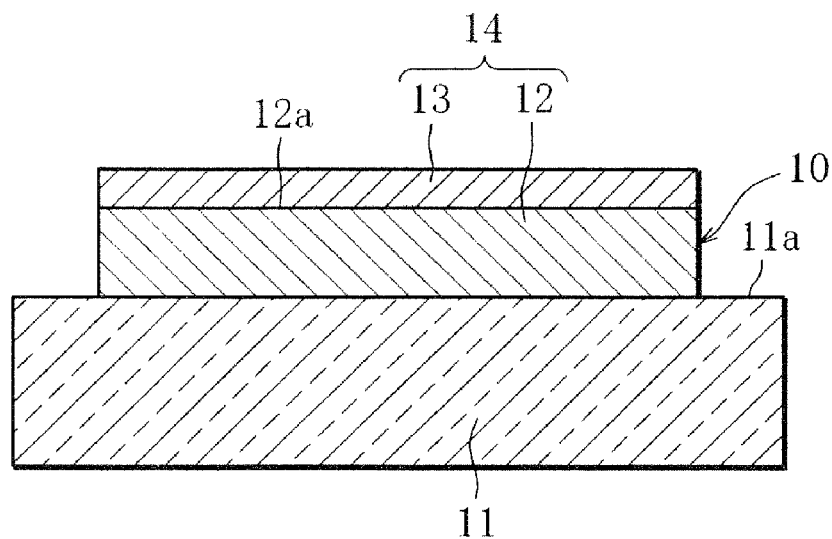
FIG. 1 schematically illustrates, in section, an exemplary construction of a hydrogen sensor according to a first embodiment of the present invention.
Figure 2:
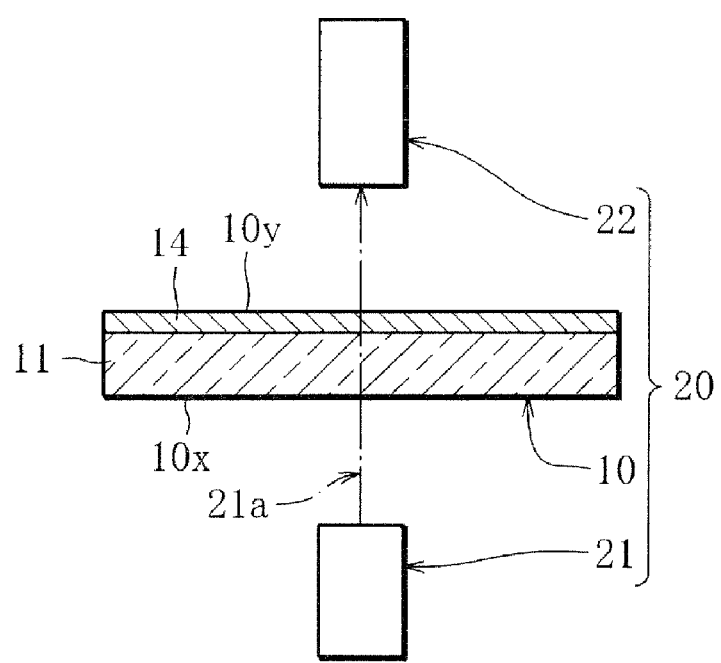
FIG. 2 schematically illustrates an exemplary configuration of a hydrogen gas detection device according to the first embodiment of the present invention.

First, a hydrogen gas detection device according to a first embodiment of the present invention will be explained with reference to FIGS. 1 and 2, wherein FIG. 1 schematically illustrates, in section, an exemplary construction of a hydrogen sensor, and FIG. 2 schematically illustrates an exemplary configuration of the hydrogen gas detection device of the first embodiment.

The hydrogen sensor used in the hydrogen gas detection device will be described first.

The hydrogen sensor 10 shown in FIG. 1 has a substrate 11 made of metal, glass, acrylic resin, or polyethylene sheet (polyethylene film). A thin-film layer 12 of magnesium-nickel alloy or magnesium is formed on a surface 11a of the substrate 11. Further, a catalyst layer 13 of palladium or platinum is formed on a surface 12a of the thin-film layer 12. The thin-film layer 12 and the catalyst layer 13 constitute a reflective film 14 of the hydrogen sensor 10.

The thin-film layer 12 may be formed by sputtering, vacuum evaporation, electron-beam evaporation or plating, and the composition thereof is, for example, $MgNi_x$ ($0 \leq x < 0.6$).

The catalyst layer 13 is formed, for example, by being coated over the surface 12a of the thin-film layer 12 and has a thickness of 1 nm to 100 nm.

When the hydrogen sensor 10 having the thin-film layer 12 and the catalyst layer 13 formed in this manner is exposed to an atmosphere with a hydrogen concentration of about 100 ppm to 1% or above, the thin-film layer 12 forming part of the reflective film 14 is rapidly hydrogenated in several to approximately ten seconds. As a result, the reflectance of the thin-film layer 12 rapidly changes.

The compositions etc. of the thin-film layer 12 and the catalyst layer 13 are not limited to those mentioned above, and also the reflectance of the thin-film layer 12 is not limited to that within the range of visible light.

The hydrogen gas detection device will be now described.

FIG. 2 schematically illustrates an exemplary configuration of a hydrogen gas detection device 20 using the aforementioned hydrogen sensor 10.

The hydrogen gas detection device 20 includes the hydrogen sensor 10, a light source 21, and an optical sensor 22. The light source 21 is arranged so as to face the reverse surface 10x of the hydrogen sensor 10 and irradiates light 21a emitted, for example, from a laser diode or light emitting diode incorporated therein toward the hydrogen sensor 10.

On the other hand, the optical sensor 22 is so arranged as to face the obverse surface 10y of the hydrogen sensor 10 in alignment with an optical path of the light 21a transmitted through the hydrogen sensor 10. The optical sensor 22 includes a phototransistor or the like for receiving the light 21a transmitted through the hydrogen sensor 10 and outputs an electrical signal corresponding to the amount of light received.

In a normal state in which no leakage hydrogen gas exists around the hydrogen gas detection device 20 configured as described above, the transmittance of the reflective film 14 is low. Accordingly, the reflective film 14 of the hydrogen sensor 10 shows high reflectance and reflects the light 21a emitted from the light source 21. As a result, the electrical signal output from the optical sensor 22 has a low level.

If, on the other hand, leakage hydrogen gas reaches the vicinity of the hydrogen sensor 10, the transmittance of the reflective film 14 of the hydrogen sensor 10 increases because the catalyst layer 13 contacts with the hydrogen gas, with the result that the reflectance of the thin-film layer 12 rapidly lowers. Accordingly, the level of the electrical signal output from the optical sensor 22 rises.

By comparing the level of the electrical signal output from the optical sensor 22 with a predetermined reference value, therefore, it is possible to detect leakage of hydrogen gas. In the hydrogen gas detection device 20, the light source 21 and the optical sensor 22 may alternatively be arranged so as to face the obverse and reverse surfaces 10y and 10x, respectively, of the hydrogen sensor 10.

Figure 3:
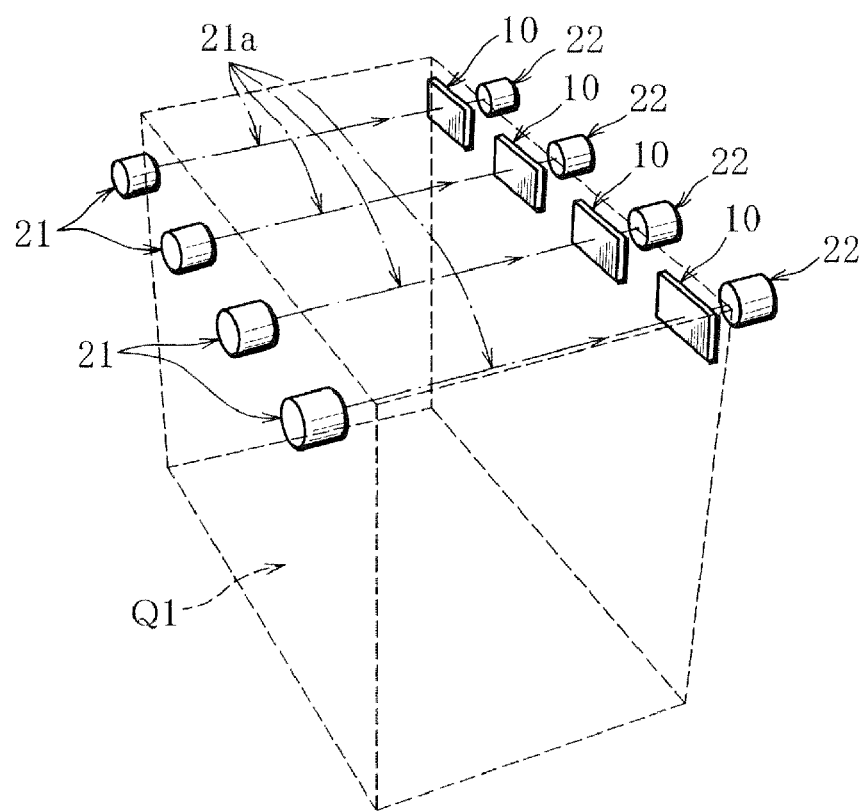
FIG. 3 illustrates an exemplary system using a plurality of hydrogen gas detection devices of the first embodiment, shown in FIG. 2.

Also, a plurality of hydrogen gas detection devices each including the hydrogen sensor 10, the light source 21 and the optical sensor 22 may be used in combination, as shown in FIG. 3. Specifically, multiple devices each comprising the hydrogen sensor 10, the light source 21 and the optical sensor 22 may be arranged in an upper region of a space Q1 (e.g., parking space of an underground parking lot) that is formed into a substantially rectangular parallelepiped, as shown in FIG. 3, for example.

In this case, the hydrogen gas detection devices are disposed such that the light beams 21a emitted from the respective light sources 21 travel in parallel with one another at regular intervals. When hydrogen gas leaking out into the space Q1 reaches the vicinity of any one of the hydrogen sensors 10, the amount of light transmitted through this hydrogen sensor 10 increases. As a result, the corresponding optical sensor 22 for detecting the light transmitted through this hydrogen sensor 10 outputs a high-level electrical signal. It is therefore possible to quickly detect leakage of hydrogen gas over a wide area.

The positional relationship of respective sets of the hydrogen sensor 10, the light source 21 and the optical sensor 22 is of course not limited to the one shown in FIG. 3.

Second Embodiment

A hydrogen gas detection device according to a second embodiment of the present invention will be now described with reference to FIG. 4. In the figure, identical reference numerals are used to denote elements with identical functions already explained with reference to the first embodiment, and description of such elements is omitted.

Figure 4:
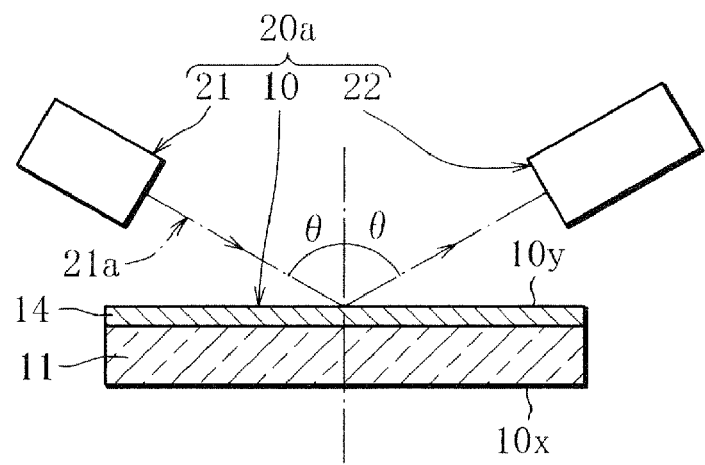
FIG. 4 schematically illustrates an exemplary configuration of a hydrogen gas detection device according to a second embodiment of the present invention.

FIG. 4 schematically illustrates an exemplary configuration of the hydrogen gas detection device 20a according to the second embodiment. In this hydrogen gas detection device 20a, the light source 21 and the optical sensor 22 are both arranged on the same side as the obverse surface 10y of the hydrogen sensor 10.

The light 21a emitted from the light source 21 falls upon the reflective film 14 of the hydrogen sensor 10 at an incidence angle θ, as shown in FIG. 4, then is reflected at the reflective film 14 and reaches the optical sensor 22. In the normal state in which no leakage hydrogen gas exists, the reflective film 14 of the hydrogen sensor 10 has high reflectance with respect to the light 21a emitted from the light source 21. Accordingly, the optical sensor 22, which receives the reflected light, outputs a high-level electrical signal.

On the other hand, if leakage hydrogen gas reaches the vicinity of the hydrogen sensor 10, the reflectance of the reflective film 14 of the sensor 10 rapidly drops. Thus, the amount of light 21a reflected by the reflective film 14 decreases, with the result that the level of the electrical signal output from the optical sensor 22 lowers.

Accordingly, by comparing the level of the electrical signal output from the optical sensor 22 with a predetermined reference value in the hydrogen gas detection device 20a, it is possible to detect leakage of hydrogen gas.

The hydrogen sensor 10 to be used in the first and second embodiments is not limited to the illustrated one and may be modified in many ways without departing from the spirit of the present invention.

For example, the reflective film is not limited to the one whose reflectance lowers upon contact with hydrogen gas. A different type of reflective film may also be used of which the reflectance is, for example, low in the normal state in which no leakage hydrogen gas exists and increases upon contact with hydrogen gas.

Also, where the substrate 11 used in the hydrogen gas detection device 20a transmits the light therethrough, the light source 21 and the optical sensor 22 may be arranged on the same side as the reverse surface 10x of the hydrogen sensor 10. Further, where the substrate 11 does not transmit the light therethrough and has low reflectance, the light source 21 and the optical sensor 22 may be arranged on the same side as the reflective film 14 (on the obverse side 10y of the hydrogen sensor 10).

Third Embodiment

A hydrogen gas detection device according to a third embodiment of the present invention will be now described with reference to FIG. 5. In the figure, identical reference numerals are used to denote elements with identical functions already explained with reference to the foregoing embodiments, and description of such elements is omitted.

Figure 5:
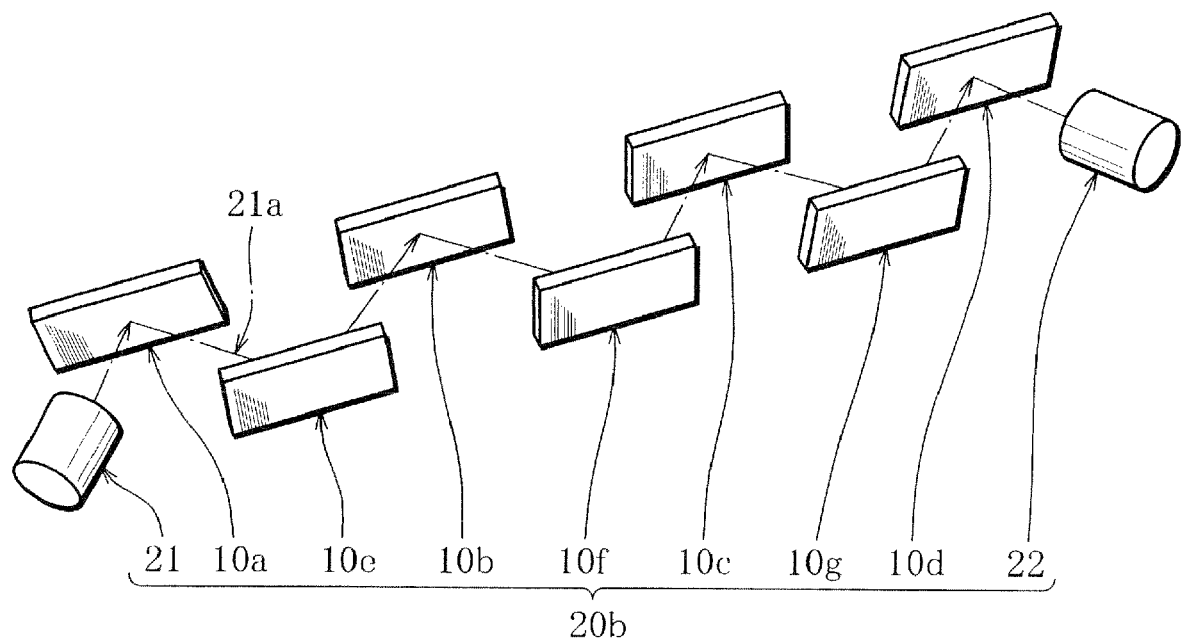
FIG. 5 schematically illustrates an exemplary configuration of a hydrogen gas detection device according to a third embodiment of the present invention.

FIG. 5 schematically illustrates an exemplary configuration of the hydrogen gas detection device 20b according to the third embodiment. The hydrogen gas detection device 20b includes a set of four hydrogen sensors 10a to 10d arranged on an identical plane, and another set of three hydrogen sensors 10e to 10g arranged on a different plane parallel with the first-mentioned plane. The light source 21, the hydrogen sensors 10a to 10g and the optical sensor 22 are positioned such that the light 21a emitted from the light source 21 is reflected successively by the hydrogen sensors 10a, 10e, 10b, 10f, 10c, 10g and 10d and reaches the optical sensor 22.

In the normal state in which no leakage hydrogen gas exists around the hydrogen gas detection device 20b, the individual reflective films 14 of the hydrogen sensors 10a to 10g have high reflectance. Accordingly, the light 21a emitted from the light source 21 reaches the optical sensor 22, which then outputs a high-level electrical signal.

On the other hand, if leakage hydrogen gas reaches the vicinity of any one of the hydrogen sensors 10a to 10g, the reflectance of the reflective film 14 of this hydrogen sensor rapidly drops. Accordingly, the amount of light received by the optical sensor 22 decreases, so that the electrical signal output from the optical sensor 22 lowers.

Thus, by comparing the level of the electrical signal output from the optical sensor 22 with a predetermined reference value in the hydrogen gas detection device 20b, it is possible to detect leakage of hydrogen gas. Also, the use of multiple hydrogen sensors enables the hydrogen gas detection device 20b to quickly detect leakage of hydrogen gas over a wide area.

The arrangement of the light source 21, the hydrogen sensors 10 and the optical sensor 22 as well as the number of hydrogen sensors are not limited to the arrangement and the number explained above with reference to the third embodiment.

Figure 6:
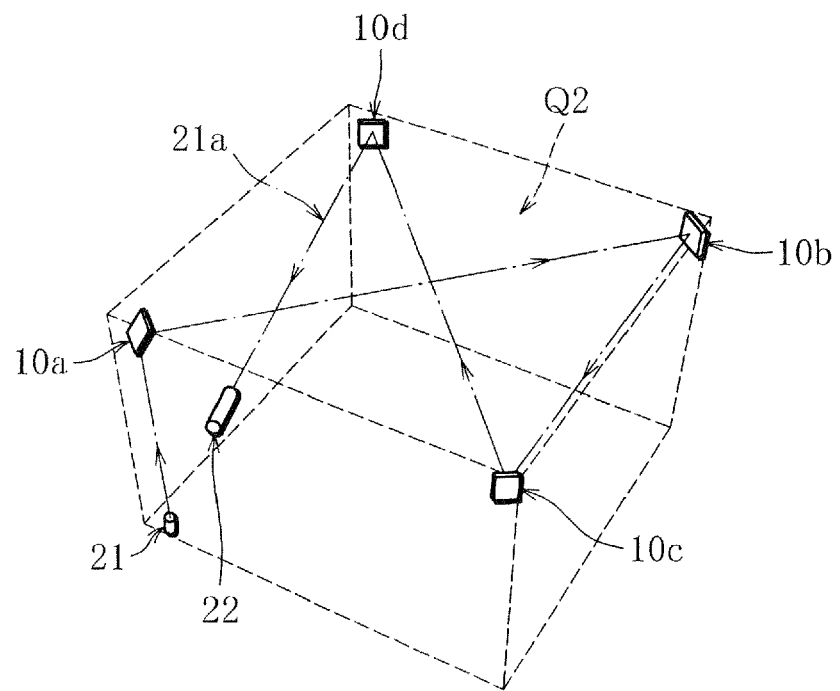
FIG. 6 illustrates another exemplary arrangement of the hydrogen gas detection device of the third embodiment.

As shown in FIG. 6, for example, the light source 21 may be arranged at one of the four lower corners of a space Q2 that is formed into a substantially rectangular parallelepiped, and four hydrogen sensors 10a to 10d may be arranged at the respective upper corners of the space Q2. Thus, in this case, the hydrogen gas detection device is configured such that the light 21a emitted upward from the light source 21 is reflected successively by the hydrogen sensors 10a to 10d to fall upon the optical sensor 22 located at an upper portion of one of the faces defining the space Q2.

More hydrogen sensors 10 than illustrated may be used to guide the light 21a emitted from the light source 21 to the optical sensor 22, and in this case, leakage of hydrogen gas can be quickly detected over a wider area.

Fourth Embodiment

A hydrogen gas detection device according to a fourth embodiment of the present invention will be now described with reference to FIG. 7. In the figure, identical reference numerals are used to denote elements with identical functions already explained with reference to the foregoing embodiments, and description of such elements is omitted.

Figure 7:
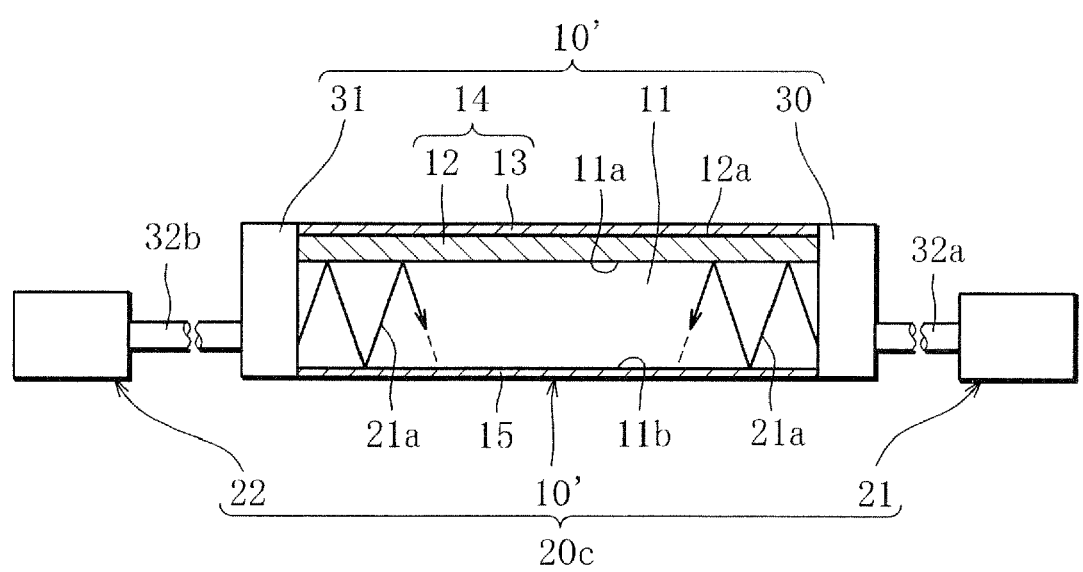
FIG. 7 schematically illustrates an exemplary configuration of a hydrogen gas detection device according to a fourth embodiment of the present invention.

FIG. 7 schematically illustrates an exemplary configuration of the hydrogen gas detection device 20c according to the fourth embodiment. The hydrogen gas detection device 20c has a hydrogen sensor 10' in which the thin-film layer 12 is formed on the obverse surface 11a of the substrate 11. Further, the catalyst layer 13 is formed on the surface 12a of the thin-film layer 12. When the catalyst layer 13 is exposed to hydrogen gas, the thin-film layer 12 is hydrogenated by the action of the catalyst layer 13, with the result that the reflectance of the thin-film layer 12 rapidly lowers. The substrate 11 has a reverse surface 11b coated with a second reflective film 15 having high reflectance. The thin-film layer 12 and the catalyst layer 13 constitute the first reflective film 14 of the hydrogen sensor 10'.

An optical input port 30 is joined to the right-hand end of the hydrogen sensor 10' as viewed in FIG. 7, and an optical output port 31 is joined to the left-hand end of the sensor 10'. The optical input port 30 is connected with an optical fiber 32a for admitting the light 21a emitted from the light source 21 into the optical input port 30. The light 21a thus admitted to the optical input port 30 is input to (guided into) the substrate 11 of the hydrogen sensor 10', then reflected alternately by the first and second reflective films 14 and 15 while propagating through the substrate 11, and reaches the optical output port 31. The light 21a arriving at the optical output port 31 is then transmitted to the optical sensor 22 through an optical fiber 32b connected to the optical output port 31.

In the normal state in which no leakage hydrogen gas exists around the hydrogen gas detection device 20c, the first reflective film 14 of the hydrogen sensor 10' has high reflectance. Accordingly, the light 21a propagates through the substrate 11 while being repeatedly reflected by the first and second reflective films 14 and 15 and reaches the optical output port 31.

On the other hand, if leakage hydrogen gas reaches the vicinity of the hydrogen sensor 10', the reflectance of the first reflective film 14 rapidly lowers. Consequently, the light 21a is eventually transmitted through the first reflective film 14 and fails to reach the optical output port 31.

Thus, by comparing the level of the electrical signal output from the optical sensor 22 with a predetermined reference value in the hydrogen gas detection device 20c, it is possible to quickly detect leakage of hydrogen gas on the basis of a drop in the amount of light 21a arriving at the optical sensor 22.

In this case, as the number of times the light 21a is reflected by the first reflective film 14 increases, the amount of light 21a arriving at the optical output port 31 shows a greater change in response to change in the reflectance of the first reflective film 14, so that the detection sensitivity of the hydrogen gas detection device 20c improves.

Where the second reflective film 15 is constituted by the thin-film layer 12 and the catalyst layer 13, like the first reflective film 14, the reflectance of the second reflective film 15 also decreases on contact with hydrogen gas, so that the hydrogen gas detection sensitivity further improves.

In the hydrogen gas detection device 20c, the light 21a is input to and output from the hydrogen sensor 10' through the respective optical fibers 32a and 32b, and there is no object that obstructs the propagation of the light 21a. Thus, the hydrogen sensor 10', the light source 21 and the optical sensor 22 can be positioned with high flexibility. Alternatively, the light source 21 may be connected directly to the optical input port 30 of the hydrogen sensor 10', and also the optical sensor 22 may be connected directly to the optical output port 31 of the hydrogen sensor 10'.

The hydrogen sensor 10' to be used in the hydrogen gas detection device 20c of this embodiment is not limited to the aforementioned one and may be modified in many ways without departing from the spirit of the invention. For example, the first reflective film 14 of the hydrogen sensor may have such reflectance that the reflectance is low in the normal state in which no leakage hydrogen gas exists and increases upon contact with hydrogen gas.

Also, instead of forming the reflective film 15 of the hydrogen sensor 10' by coating, a material that hardly absorbs light may be bonded to the substrate 11. Light is reflected at the reflection interface between the reverse surface 11b of the substrate 11 and the corresponding surface of the bonded material, and the reflection interface functions as a reflection surface only if the bonded material has a predetermined thickness or more. Thus, it can be said that the predetermined thickness of the bonded material constitutes the reflective film. The reflective film 15 can therefore be formed by bonding a material that hardly absorbs light to the substrate 11.

Fifth Embodiment

A hydrogen gas detection device according to a fifth embodiment of the present invention will be now described with reference to FIG. 8. In the figure, identical reference numerals are used to denote elements with identical functions already explained with reference to the foregoing embodiments, and description of such elements is omitted.

Figure 8:
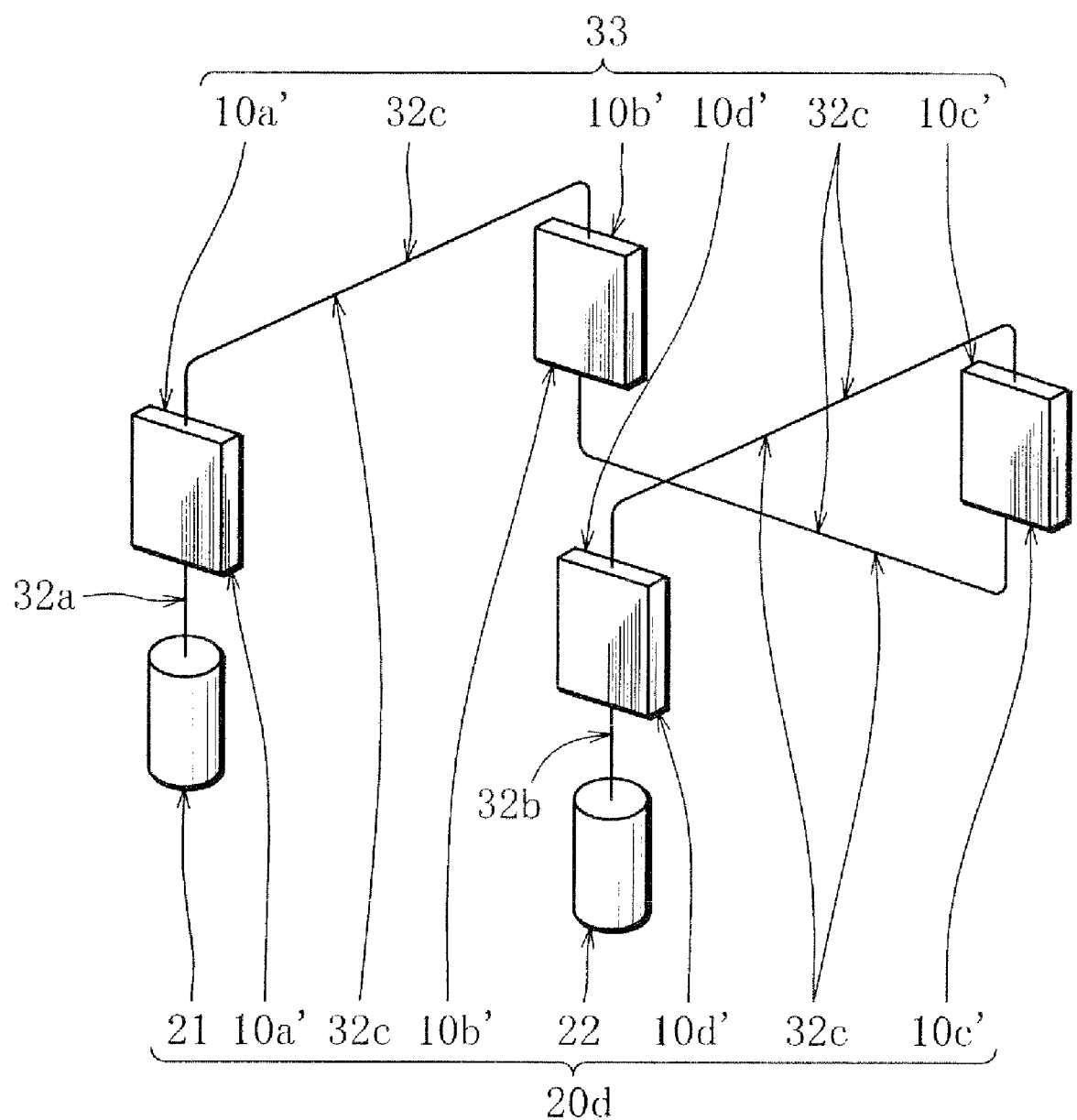
FIG. 8 schematically illustrates an exemplary configuration of a hydrogen gas detection device according to a fifth embodiment of the present invention.

The hydrogen gas detection device 20d shown in FIG. 8 includes four hydrogen sensors 10a' to 10d' (each having a construction identical with that of the hydrogen sensor 10'). The four hydrogen sensors 10a' to 10d' are arranged at respective different locations and are cascade-connected by three optical fibers (optical transmission means) 32c to form an optical circuit 33.

In the hydrogen gas detection device 20d, the light 21a emitted from the light source 21 is input to the optical circuit 33 through the optical fiber 32a connected to the optical input port 30 of the hydrogen sensor 10a' situated at the input end of the optical circuit 33. The input light 21a is propagated through the optical circuit 33 and output from the optical output port 31 of the hydrogen sensor 10d' situated at the output end of the optical circuit 33. The light 21a thus output from the optical output port 31 is transmitted through the optical fiber 32b to the optical sensor 22.

The hydrogen sensors 10a' to 10d' are arranged, for example, in an upper region of the parking space of an underground parking lot to detect leakage of hydrogen gas from the hydrogen fuel cell vehicles parked in the parking space.

In the normal state in which no leakage hydrogen gas exists around the hydrogen gas detection device 20d, the first reflective films 14 of the hydrogen sensors 10a' to 10d' each have high reflectance. Accordingly, the light 21a can reach the optical output port 31 of the hydrogen sensor at the output end.

On the other hand, if leakage hydrogen gas reaches the vicinity of any one of the hydrogen sensors 10a' to 10d', the reflectance of the first reflective film 14 of this hydrogen sensor rapidly drops. Consequently, the amount of light 21a reaching the optical sensor 22 decreases.

Thus, by comparing the level of the electrical signal output from the optical sensor 22 with a predetermined reference value in the hydrogen gas detection device 20d, it is possible to quickly detect leakage of hydrogen gas on the basis of a drop in the amount of light 21a reaching the optical sensor 22.

Also, in the hydrogen gas detection device 20d, the light 21a is input to and output from the individual hydrogen sensors 10a' to 10d' through the optical fibers 32a, 32b and 32c, and there is no object that obstructs the propagation of the light 21a from the light source 21. Accordingly, the hydrogen sensors 10a' to 10d', the light source 21 and the optical sensor 22 can be arranged with high flexibility.

The hydrogen sensors 10a' to 10d' to be used in the hydrogen gas detection device 20d of the fifth embodiment are not limited to the aforementioned one and may be modified in many ways without departing from the spirit of the invention.

For example, the second reflective film 15 may have a layered structure identical with that of the first reflective film 14 so that the reflectance of the second reflective film 15 may also lower upon contact with hydrogen gas.

Further, although in the hydrogen gas detection device 20d of the fifth embodiment, the four hydrogen sensors are cascade-connected by the optical transmission means, the configuration of the optical circuit is not limited to the illustrated one alone. For example, the light emitted from a single light source may be split to be input to a plurality of optical circuits each including cascade-connected hydrogen sensors, and each optical circuit may be connected with an optical sensor.

The present invention is of course not limited to the foregoing embodiments alone and may be modified in various ways without departing from the spirit of the invention.

The invention claimed is:

1. A hydrogen gas detection device comprising:
a hydrogen sensor including a substrate capable of transmitting light therethrough,
a first reflective film formed on one surface of the substrate,
a second reflective film formed on an opposite surface of the substrate,
an optical input port for admitting light to one end of the substrate, and
an optical output port for receiving the light that arrives at an opposite end of the substrate after being input from the optical input port and then reflected alternately by the first and second reflective films, and for allowing the received light to be output to outside of the substrate, wherein reflectance of either one or both of the first and second reflective films varies upon contact with hydrogen gas;
a light source for inputting the light to the optical input port; and
an optical sensor for receiving the light output from the optical output port and outputting a detection signal;
wherein the first and/or second reflective film of which the reflectance varies upon contact with hydrogen gas includes:
a thin-film layer formed on the corresponding surface of the substrate; and
a catalyst layer formed on a surface of the thin-film layer, the catalyst layer hydrogenating the thin-film layer upon contact with hydrogen gas to vary reflectance of the thin-film layer.

2. A hydrogen gas detection device comprising:
a plurality of hydrogen sensors each including a substrate capable of transmitting light therethrough, a first reflective film formed on one surface of the substrate, a second reflective film formed on an opposite surface of the substrate, an optical input port for admitting light to one end of the substrate, and an optical output port for receiving the light that arrives at an opposite end of the substrate after being input from the optical input port and then reflected alternately by the first and second reflective films, and for allowing the received light to be output to outside of the substrate, wherein reflectance of either one or both of the first and second reflective films varies upon contact with hydrogen gas;
optical transmission means for cascade-connecting the hydrogen sensors to form an optical circuit;
a light source for inputting the light to the optical input port of that one of the cascade-connected hydrogen sensors which is situated at input end of the optical circuit; and
an optical sensor for receiving the light output from the optical output port of that one of the cascade-connected hydrogen sensors which is situated at an output end of the optical circuit, and for outputting a detection signal.

3. The hydrogen gas detection device according to claim 2, wherein the first and/or second reflective film of which the reflectance varies upon contact with hydrogen gas includes:
a thin-film layer formed on the corresponding surface of the substrate; and
a catalyst layer formed on a surface of the thin-film layer, the catalyst layer hydrogenating the thin-film layer upon contact with hydrogen gas to vary reflectance of the thin-film layer.

* * * * *